(12) United States Patent
Hussain et al.

(10) Patent No.: US 9,625,403 B1
(45) Date of Patent: Apr. 18, 2017

(54) METHOD OF ASCERTAINING FULLY GROWN PASSIVE FILM FORMATION ON STEEL REBAR EMBEDDED IN CONCRETE

(71) Applicant: KING SAUD UNIVERSITY, Riyadh (SA)

(72) Inventors: Raja Rizwan Hussain, Riyadh (SA); Abdulrahman Alhozaimy, Riyadh (SA); Abdulaziz Al-Negheimish, Riyadh (SA); DDN Singh, Jamshedpur (IN)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/872,081

(22) Filed: Sep. 30, 2015

(51) Int. Cl.
*G01N 27/02* (2006.01)
*G01N 17/02* (2006.01)
*G01N 33/20* (2006.01)

(52) U.S. Cl.
CPC ........... *G01N 27/026* (2013.01); *G01N 17/02* (2013.01); *G01N 33/20* (2013.01)

(58) Field of Classification Search
CPC ...... G01N 17/02; G01N 17/04–17/046; G01N 17/026; G01N 27/026; G01N 33/20
See application file for complete search history.

(56) References Cited

U.S. PATENT DOCUMENTS

| | | |
|---|---|---|
| 5,674,375 A | 10/1997 | Thompson |
| 5,895,843 A | 4/1999 | Taylor et al. |
| 6,805,788 B1 | 10/2004 | Gonzalez-Martin et al. |
| 7,088,115 B1 | 8/2006 | Glenn et al. |
| 2008/0179198 A1 | 7/2008 | Burgess et al. |

FOREIGN PATENT DOCUMENTS

CN 102706933 A 10/2012

OTHER PUBLICATIONS

M. Sanchez, Anodic growth of passive layers on steel rebars in an alkaline medium simulating the concrete pores, Electrochimica Acta, vol. 52, pp. 47-53 (2006).*

(Continued)

*Primary Examiner* — Luan Van
*Assistant Examiner* — Maris R Kessel
(74) *Attorney, Agent, or Firm* — Richard C. Litman

(57) ABSTRACT

The method of ascertaining fully grown passive film formation on steel rebar embedded in concrete utilizes electrochemical impedance spectroscopy (EIS) to determine, in situ, the degree of passive film formation on steel rebar embedded in concrete. A length of steel rebar and a counter electrode are both embedded in a concrete slab. A reservoir is supported on an external face of the concrete slab and filled with an electrolytic solution. A reference electrode is then positioned in the electrolytic solution, and the length of steel rebar, the counter electrode and the reference electrode are electrically connected an EIS test instrument to perform electrochemical impedance spectroscopy. The quality of passive film formation on the length of steel rebar is determined based on comparison of the electrochemical impedance spectroscopy results with known passive film formation data.

2 Claims, 3 Drawing Sheets

(56) References Cited

OTHER PUBLICATIONS

J. M. Deus, et al., The electrochemical behaviour of steel rebars in concrete:an Electrochemical Impedance Spectroscopy study of theeffect of temperature, Electrochimica Acta, vol. 131, pp. 106-115 (available online Dec. 16, 2013).*

Abreu et al., "High Frequency Impedance Spectroscopy study of Passive Films Formed on AISI 316 Stainless Steel in Alkaline Medium," J. of Electroanalytical Chemistry, 2004, vol. 572, pp. 335-345.

Silva et al. "A Study of Steel Bar Reinforcement Corrosion in Concretes with SF and SRH Using Electrochemical Impedance Spectroscopy," Materials Research, 2006, vol. 9, pp. 209-215.

* cited by examiner

METHOD OF ASCERTAINING FULLY GROWN PASSIVE FILM FORMATION ON STEEL REBAR EMBEDDED IN CONCRETE

BACKGROUND OF THE INVENTION

1. Field of the Invention

The present invention relates to procedures for testing structural materials used in the construction industry, and particularly to a method of ascertaining fully grown passive film formation on steel rebar embedded in concrete using electrochemical impedance spectroscopy (EIS).

2. Description of the Related Art

Electrochemical impedance spectroscopy (EIS) (sometimes also referred to as "dielectric spectroscopy" or "impedance spectroscopy") is a technique for measuring the dielectric properties of a medium as a function of frequency. EIS is based on the interaction of an external electric field with the electric dipole moment of a sample, typically expressed by electrical permittivity. EIS is often used as an experimental method for characterizing electrochemical systems. The technique measures the impedance of a system over a range of frequencies, and therefore the frequency response of the system (including the energy storage and dissipation properties) is revealed. Typically, data obtained by EIS is expressed graphically in a Bode plot or a Nyquist plot.

FIG. 2 illustrates a conventional three-electrode electrochemical cell for electrochemical impedance measurement by EIS. Cell 100 contains an electrolyte solution 108 in which a working electrode 102 and a counter electrode 104 are immersed. Typically, the working electrode 102 and the counter electrode 104 are parallel plate electrodes. In addition to the working electrode 102 and the counter electrode 104, a third voltage reference electrode 106 is placed close to the polarization layer (i.e., the region of positive polarization 110 near the working electrode 102) and measures the voltage difference of the polarization double layer capacity to the working electrode 102. The working electrode 102 is made of the metal to be characterized in combination with the electrolyte 108. The reference electrode 106 may be, for example, an open-tipped glass capillary filled with a standard electrolyte coupled to a standard metal in order to create a defined electrochemical potential to the electrolyte.

The total potential drop across the cell is summed up by all contributions of the chemical process, including mass transport, chemical and adsorption steps, electron transfer, etc. By measuring the impedance spectrum:

$$\frac{V^*_{REF}(\omega)}{I^*_s(\omega)}$$

over angular frequency range $\omega$ and fitting it with an equivalent circuit model, the several process contributions can be separated from each other. The typical evaluation includes determination of Warburg impedance related to mass transport, electron transfer resistance, electrolyte resistance and double layer capacity. As the electrochemical reaction takes place on the working electrode 102, it is necessary to keep the DC potential $V_{REF}$ at a defined value, or alternatively, apply a constant DC current to the cell. This is often performed with a potentiostat/galvanostat DC circuit.

Electrochemical impedance spectroscopy has been used to characterize the nanoscale passive film formation on steel rebar in concrete at different stages of exposure in simulated concrete pore solution (SPS). However, since the rebar is placed in SPS, rather than an actual concrete environment, the EIS results are typically not representative of the actual behavior. It would be desirable to be able to characterize nanoscale passive film formation on steel rebar in its actual concrete environment.

Thus, a method of ascertaining fully grown passive film formation on steel rebar embedded in concrete solving the aforementioned problems is desired.

SUMMARY OF THE INVENTION

The method of ascertaining fully grown passive film formation on steel rebar embedded in concrete utilizes electrochemical impedance spectroscopy (EIS) to determine, in situ, the degree or quality of passive film formation on steel rebar embedded in concrete. A length of steel rebar and a counter electrode, such as a graphite electrode, are both embedded in a concrete slab, the counter electrode being positioned adjacent and parallel to the length of steel rebar. For electrochemical impedance spectroscopy, the length of steel rebar acts as a working electrode. A reservoir is supported on an external face of the concrete slab and filled with an electrolytic solution, such as simulated concrete pore solution. A reference electrode, such as a saturated calomel electrode, is then positioned in the electrolytic solution, and the length of steel rebar, the counter electrode and the reference electrode are electrically connected to an EIS test instrument to perform electrochemical impedance spectroscopy in order to generate a plot of impedance as a function of frequency for the coupled length of steel rebar and the counter electrode. The plot is then matched to a known plot of passive film formation on steel rebar, and a degree or quality of passive film formation on the length of steel rebar is determined based on passive film formation associated with the matched plot.

These and other features of the present invention will become readily apparent upon further review of the following specification.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
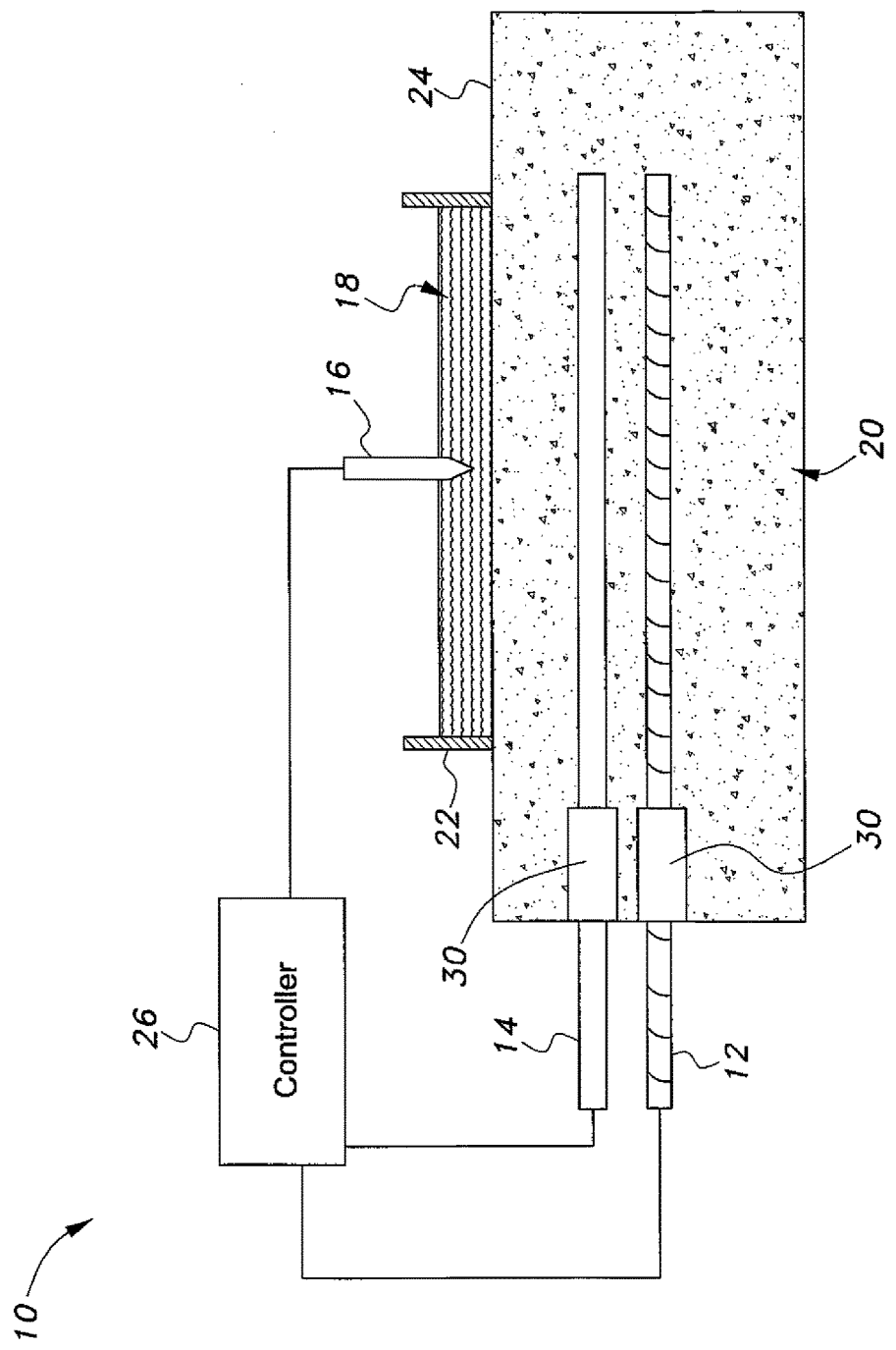
FIG. 1 is a schematic diagram illustrating a steel rebar and concrete electrochemical impedance spectroscopy cell for performing a method of ascertaining fully grown passive film formation on steel rebar embedded in concrete according to the present invention.
Figure 2:
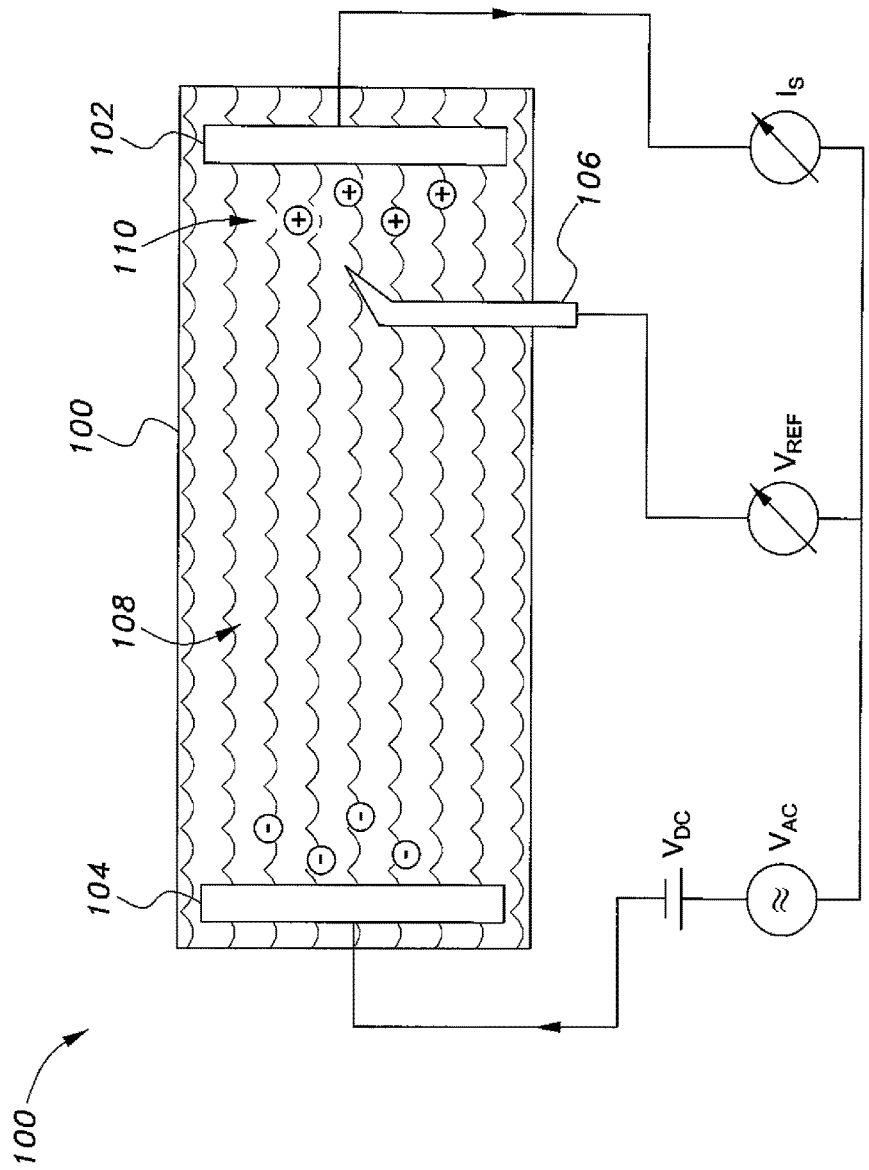
FIG. 2 is a schematic diagram illustrating a conventional prior art electrochemical impedance spectroscopy cell.

The method of ascertaining fully grown passive film formation on steel rebar embedded in concrete utilizes electrochemical impedance spectroscopy to characterize nanoscale passive film formation on steel rebar while it is embedded in its actual concrete environment. As shown in FIG. 1, a three-electrode electrochemical impedance cell 10, similar to cell 100 of FIG. 2, is established, using steel rebar 12 embedded in concrete 20 as the working electrode. A counter electrode 14, which may be formed from any suitable conductive material, such as graphite, is embedded in the concrete 20 parallel to the steel rebar working electrode 12. A reservoir 22 is supported on an external face 24 of the concrete slab 20 and contains an electrolyte solution 18. A reference electrode 16 is immersed in the electrolyte solution 18, as shown.

The reference electrode 16 may be, for example, a saturated calomel electrode (SCE). An SCE, as is well known in the art, is a reference electrode based on the reaction between elemental mercury and mercury(I) chloride. The aqueous phase in contact with the mercury and the mercury (I) chloride ($Hg_2Cl_2$ or "calomel") is a saturated solution of potassium chloride in water. The electrode is normally linked via a porous frit to the solution in which the other electrode is immersed, where the porous fit is a salt bridge. The steel rebar working electrode 12, the counter electrode 14 and the reference electrode 16 are each in electrical communication with an EIS test instrument or controller 26, which supplies voltage, measures the impedance and calculates the electrochemical impedance spectroscopy results. It should be understood that EIS test instruments are available in many different configurations, and in the drawings, controller 26 represents any suitable type EIS test instrument known in the art, which may include a computer, programmable logic controller, digital signal processor, or other data processing device programmed to perform EIS calculations and output EIS results. Using electrochemical impedance spectroscopy to measure the degree or quality of corrosion in metals is well known. An example is shown in U.S. Patent Application Publication No. 2008/0179198, which is hereby incorporated by reference in its entirety.

In use, the length of steel rebar 12 and the graphite counter electrode 14 are both embedded in a concrete slab 20, the counter electrode 14 being positioned adjacent and parallel to the length of steel rebar 12, as shown in FIG. 1. A terminal portion of each electrode 12, 14 extends from the concrete slab 20 for connection to the controller 26 by suitable wires/cables. For electrochemical impedance spectroscopy, the length of steel rebar 12 acts as a working electrode. A reservoir 22 is mounted on an external face 24 of the concrete slab 20 and filled with an electrolytic solution 18, such as simulated concrete pore solution. A reference electrode 16, such as a saturated calomel electrode, is then positioned in the electrolytic solution 18, and the length of steel rebar 12, the counter electrode 14 and the reference electrode 16 are electrically connected to the controller 26 to perform electrochemical impedance spectroscopy in order to generate a plot of impedance as a function of frequency for the coupled length of steel rebar 12 and the counter electrode 14. The plot is then matched to a known plot of passive film formation on steel rebar, and the degree or quality of passive film formation on the length of steel rebar 12 is determined based upon passive film formation associated with the matched plot.

In order to evaluate the present method, the results from the cell 10 of FIG. 1 were compared against results performed in a simulated concrete pore solution (SPS). The steel reinforcement bars used in the experiments each had lengths of 300 mm, and were descaled by abrading, followed by having their surfaces embedded in concrete. Type I cement, in compliance with the requirements of ASTM C150, was used. Coarse aggregates in the cement include a blend of 20 mm and 10 mm crushed limestone, which were obtained from quarries near Riyadh, Saudi Arabia. The fine aggregates were a blend of natural red sand and manufactured sand obtained from the crushed limestone. The mix proportions used in the concrete specimens are shown in Table 1 below.

TABLE 1

Concrete Mix Proportions

| Material | Proportions (kg/m$^3$) |
| --- | --- |
| Cement | 350 |
| 20 mm Aggregates | 735 |
| 10 mm Aggregates | 315 |
| Crushed Sand | 195 |
| Silica Sand (Red Sand) | 585 |

In the experiments, a typical water-to-cement ratio (w/e) of 0.50 was used. Standard laboratory curing conditions were used, in which standard prism specimens in plastic molds were stored in a laboratory environment at standard room temperature for the first 24 hours, followed by demolding before the start of testing. Corresponding to the diagrammatic illustration of FIG. 1, the experimental reinforced concrete prismatic specimen 20 had dimensions of 100 mm×100 mm×250 mm. As shown in FIG. 1, the first 25 mm of exposed rebar surface of each rebar electrode (adjacent the opening edge of the concrete specimen 20) was blocked with a tight cover of Teflon® tape 30, secured with a layer of epoxy resin. These end blocks 30 ensured a crevice-free entering end of each rebar electrode in the concrete specimen 20. After demolding the specimen, the pond reservoir 22 was made atop the concrete 20, filled with the simulated concrete pore solution (i.e., the electrolytic solution 18) for use in the electrochemical impedance studies. Open circuit potentials and electrochemical impedance spectra were evaluated via controller 26 every 24 hours for a period of 32 days.

Figure 3:
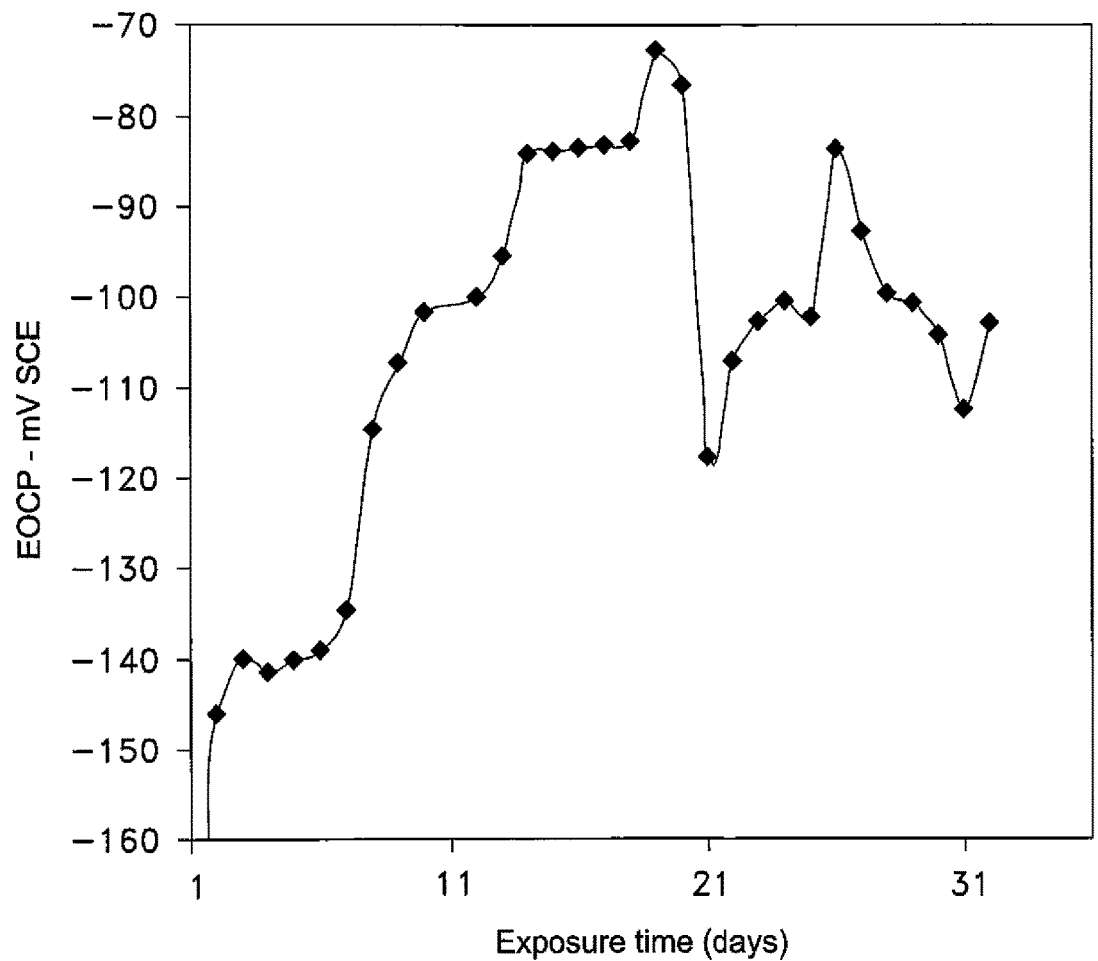
FIG. 3 is an exemplary graph showing measured potential as a function of time for a length of steel rebar embedded in concrete using the method of ascertaining fully grown passive film formation on steel rebar embedded in concrete according to the present invention.

A set of data were generated from the reinforcement bar samples embedded in solid concrete, as described above, and the resultant potential vs. time plot is shown in FIG. 3. Here, the changes in corrosion potentials developed at the concrete-rebar interfaces were monitored for 32 days. As can be seen in FIG. 3, a systematic ennobling in potential over time takes place up to 20 days of exposure. Beyond this period, the change is relatively slow with movement of potentials in the active direction.

The initial shift of potential (in the nobler direction) is attributed to the thickening of the oxide, resulting in anodic polarization of the reaction taking place at the rebar/concrete interface. The fluctuation of the potential in the active direction beyond 20 days is most likely due to cathodic polarization caused by the limited supply of oxygen at the interface. After initial hydration and other reactions, concrete becomes denser with the passage of time after casting, which limits the supply of oxygen at the rebar/concrete interface, resulting in polarization of cathodic reaction.

It can be further seen in FIG. 3 that the drifting of the potential remains mostly in the range of −90 mV to −120 mV. As per ASTM C876-09, this potential is in the range of protective potential for steel exposed in concrete. These results reveal the passive film on steel rebars becomes a fully protective film after 20 days of exposure. This period is longer than the protective potential attained by the rebar exposed to SPS. These results suggest that the film formation and growth is slower in solid concrete compared to the simulated pore solution. The presence of a higher content of oxygen and alkalinity in the simulated pore solution in comparison to solid concrete may have contributed to the rapid nucleation and growth of the passive film in the case of rebars exposed to SPS.

It is to be understood that the present invention is not limited to the embodiments described above, but encompasses any and all embodiments within the scope of the following claims.

We claim:

1. A method of ascertaining in situ fully grown passive film formation on steel rebar embedded in concrete by analyzing both open circuit potentials and electrochemical impedance spectra (EIS), the method consisting of:
    embedding a length of steel rebar in a concrete slab to form a working electrode;
    embedding a graphite counter electrode in the concrete slab, the counter electrode being positioned adjacent and parallel to the length of steel rebar;
    supporting a reservoir on an external face of the concrete slab;
    filling the reservoir with an electrolytic solution with simulated concrete pore solution;
    immersing a reference electrode in the electrolytic solution, wherein the working electrode, the graphite counter electrode, the concrete slab, and the reference electrode immersed in electrolytic solution defining a three-electrode electrochemical impedance spectroscopy (EIS) test cell adapted for connection to an EIS test instrument;
    electrically connecting the electrodes to the EIS test instrument;
    obtaining data from open circuit potentials;
    performing and obtaining data from electrochemical impedance spectroscopy to generate a plot of impedance as a function of frequency for the length of steel rebar and the counter electrode;
    matching the plot to a known plot of passive film formation on steel rebar and reviewing the data obtained from the open circuit potentials; and
    determining a degree of passive film formation on the length of steel rebar in situ based on passive film formation associated with the matched plot.

2. The method of ascertaining fully grown passive film formation on steel rebar embedded in concrete as recited in claim 1, wherein the reference electrode comprises a saturated calomel electrode.

* * * * *